US006668189B2

(12) United States Patent
Kaiser et al.

(10) Patent No.: US 6,668,189 B2
(45) Date of Patent: Dec. 23, 2003

(54) METHOD AND SYSTEM FOR MEASURING T-WAVE ALTERNANS BY ALIGNMENT OF ALTERNATING MEDIAN BEATS TO A CUBIC SPLINE

(75) Inventors: Willi Kaiser, Emmendingen (DE); Martin Findeis, Freiburg (DE)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 49 days.

(21) Appl. No.: 09/682,698

(22) Filed: Oct. 5, 2001

(65) Prior Publication Data

US 2003/0069512 A1 Apr. 10, 2003

(51) Int. Cl.[7] .............................. A61B 5/0472
(52) U.S. Cl. ....................... 600/518; 600/517
(58) Field of Search ................. 600/517, 518, 600/515

(56) References Cited

U.S. PATENT DOCUMENTS

| | | | | |
|---|---|---|---|---|
| 4,802,491 A | * | 2/1989 | Cohen et al. | 600/515 |
| 5,148,812 A | | 9/1992 | Verrier et al. | 128/704 |
| 5,570,696 A | * | 11/1996 | Arnold et al. | 600/520 |
| 5,921,940 A | | 7/1999 | Verrier et al. | 600/518 |
| 6,169,919 B1 | | 1/2001 | Nearing et al. | 600/518 |
| 2003/0060724 A1 | * | 3/2003 | Thiagarajan et al. | 600/515 |

OTHER PUBLICATIONS

Armoundas, et al.; Clinical Utility of T–Wave Alternans; Cardiac Electrophysiology Review; vol. 3; pp. 390–394, 1997.
CH 2000, Physician's Guide to Alternans; Rev. F, Cambridge Heart, pp. 1–1 thru 10–2.
Rosenbaum et al.; Electrical Alternans and Vulnerability to Ventricular Arrhythmias; The New England Journal of Medicine; vol. 330; pp. 235–241; Jan. 27, 1994.
Verrier, et al.; Physiology of Electrical Alternans; Cardiac Electrophysiology Review, vol. 3; pp. 381–386, 1997.

* cited by examiner

Primary Examiner—Kennedy Schaetzle
(74) Attorney, Agent, or Firm—Fletcher Yoder

(57) ABSTRACT

An electrocardiogram processing technique for measuring T-wave alternans by which the alternating electrocardiogram signals are aligned to a target cubic spline. The target cubic spline is calculated on base of three isoelectric points namely a point before the P-wave, a point before the QRS-complex and a point after the T-wave. The aligned signals may then be further analyzed for variations such as T-wave alternans which are only present in alternating beats and which have diagnostic significance.

61 Claims, 5 Drawing Sheets

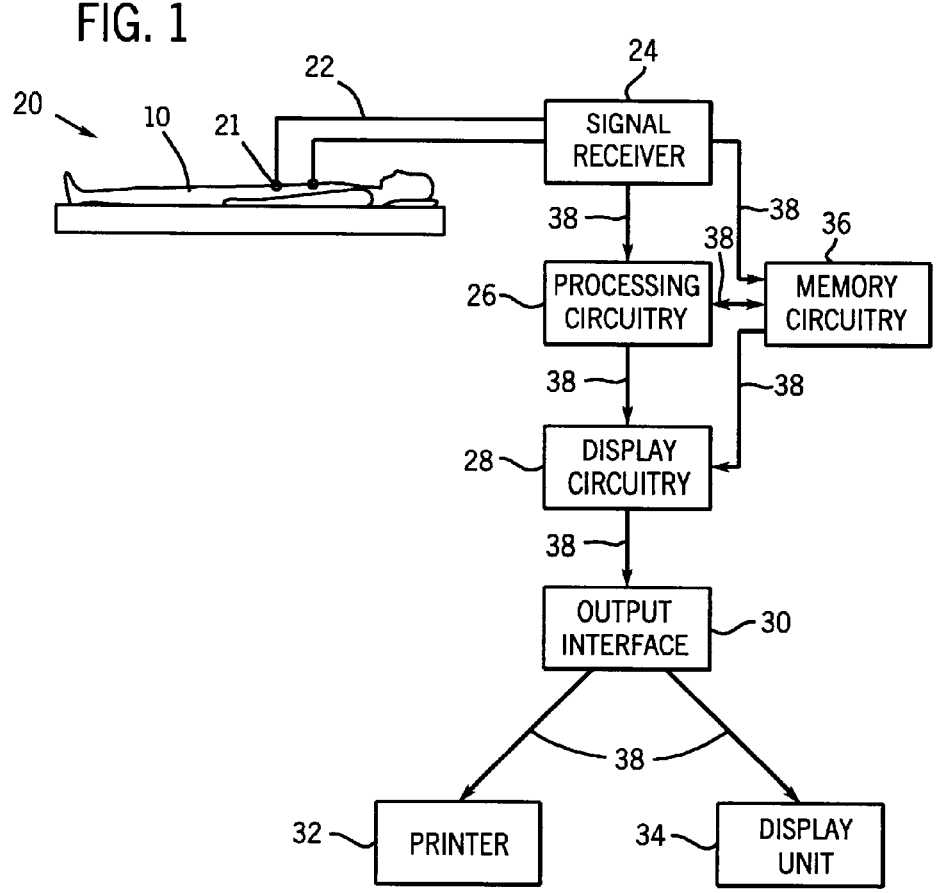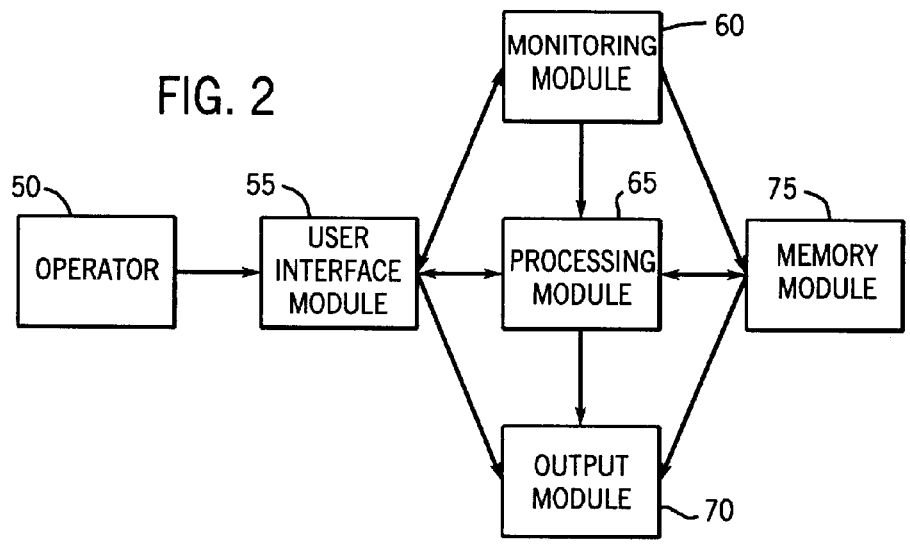

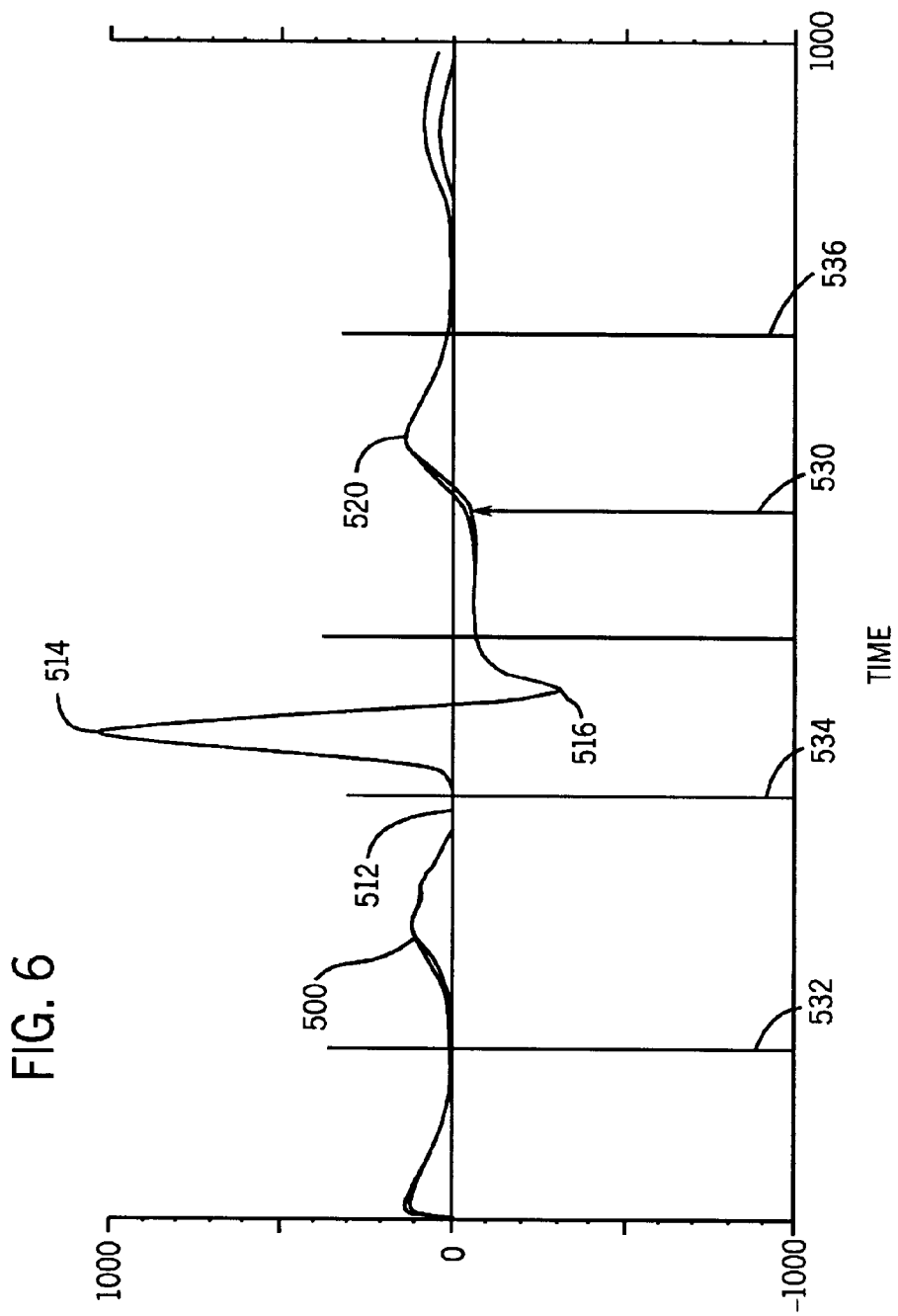

METHOD AND SYSTEM FOR MEASURING T-WAVE ALTERNANS BY ALIGNMENT OF ALTERNATING MEDIAN BEATS TO A CUBIC SPLINE

BACKGROUND OF INVENTION

The present invention relates generally to the field of cardiology and, more particularly, to a method and system of processing an electrocardiogram signal to detect T-wave alternans by aligning alternating beats to a cubic spline. More accurate detection and quantification of alternans within the ST-segment and T-wave of the signal is then possible upon the aligned beats.

In the field of electrocardiography, electrical alternans are the differences in electrical potential at corresponding points between alternate heartbeats. T-wave alternans or alternation is a regular beat-to-beat variation of the ST-segment or T-wave of an ECG which repeats itself every two beats and has been linked to underlying cardiac instability. A patient's odd and even heartbeats may therefore exhibit different electrical properties of diagnostic significance which can be detected by an electrocardiogram (ECG).

The presence of these electrical alternans is significant because patients at increased risk for ventricular arrythmias commonly exhibit alternans in the ST-segment and the T-wave of their ECG. Clinicians may therefore use these electrical alternans as a noninvasive marker of vulnerability to ventricular tacharrhythmias. The term T-wave alternans (TWA) is used to broadly denote these electrical alternans. It should be understood that the term encompasses both the alternans of the T-wave segment and the ST-segment of an ECG.

It may however be both difficult to detect TWA and difficult to quantify the magnitude of TWA since the magnitude of the phenomena is typically less than one hundred microvolts. Differences of this magnitude between ECG signals are difficult to differentiate from baseline wander, white noise, or from other artifacts such as patient movement or other irregularities in the heartbeat.

The current method of detecting TWA involves receiving an ECG signal and, from this data, calculating both an odd and an even median complex using the respective incoming odd and even signal data. The odd median complex is then compared with the even median complex to obtain an estimate of the amplitude of beat-to-beat alternation in the ECG data. The maximum alternation amplitude observed between the end of the QRS-complex and the end of the T wave is defined as the T-wave alternans value. A TWA is present if this value is greater than some threshold value determined by a clinician.

In the prior art the baseline wander was removed by calculating a cubic spline based on points measured between the P-wave and the QRS-complex of three consecutive QRS complexes. The values generated by this spline curve were then subtracted from the corresponding values of the incoming beat data. Since points in the isoelectric area preceding the QRS complex are used to calculate the cubic spline, this method does not properly correct for baseline wander between the end of the QRS-complex and the end of the T-wave.

To better correct baseline wander it would be preferable to use an additional point after the T-wave in calculating the cubic spline correction. However the amplitudes of the isoelectric areas before the QRS-complex and between the T and P-waves differ. The isoelectric area before the QRS-complex is influenced by the atrial repolarisation. Other reasons for different amplitudes in both "isoelectric areas" could be a short PR-interval or a merging of P- and T-waves. Applying the cubic spline correction algorithm to points before the QRS-complex and also to points after the T-wave will cause the algorithm to produce artificial baseline wander, and therefore to produce incorrect T-wave alternans values. As a result, a more effective means of aligning odd and even heartbeats is needed in order to obtain more accurate TWA values.

SUMMARY OF INVENTION

The invention offers a technique for detecting T-wave alternans by aligning alternating heartbeat data, i.e. odd and even beats. In a preferred embodiment of the invention, a digitized ECG signal is received for processing. The ECG data is used to calculate an odd and even median beat and a target cubic spline which is then used to align an odd and an even median beat complex. The odd median complex is then compared with the even median complex to obtain an estimate of the amplitude of beat-to-beat alternation in the ECG signal.

The step of calculating a median complex may proceed as follows. A first array (representing the odd median complex) is initialized with the median of a plurality of odd complex values. A second array (representing the even median complex) is initialized with the median of a plurality of even complex values. The samples of a new odd beat of the ECG data are compared to corresponding values in the first array and, based on the comparison, the values of the first array are adjusted as follows. If a sample of the odd beat exceeds the corresponding value of the first array by a fixed amount, then the corresponding value is incremented by the fixed amount. In the other case the corresponding value is incremented by $\frac{1}{32}$th of the difference between the sample of the odd beat and the corresponding value of the first array This process is repeated for other odd beats desired to be included in the calculation. This same process is then followed for the second array using the even beats.

Once the odd and even median complexes have been calculated they are then aligned. This alignment is accomplished by calculating a target cubic spline, an odd median complex cubic spline, and an even median complex cubic spline. The differences between the target cubic spline and both the odd median complex cubic spline and the even median complex cubic spline are then calculated. These differences are then subtracted, respectively, from the odd and even median beat data, to correct (align) them.

The effect of this alignment step is to minimize any residual baseline wander between the odd and even beat data. More accurate comparisons of the odd and even beat data may then be made.

In accordance with one aspect of the present technique, there is provided a method of calculating a reference function (in the preferred embodiment a target cubic spline) derived from odd and even beat data and useful for aligning odd and even median beat complexes.

In accordance with another aspect of the present technique, there is provided a method of processing ECG signals for alternating heartbeats and of aligning these alternating heartbeats using cubic splines. The method may be extended to incorporate the detection and quantification of differences, such as alternans, between the alternating ECG signals.

In accordance with another aspect of the present technique, there is provided a system for processing ECG signals for alternating heartbeats whereby the ECG signals are analyzed by processing circuitry to derive a reference function, the alternating ECG signals are aligned by the processing circuitry, and the aligned ECG signals are saved by memory circuitry or displayed by display circuitry. In addition, the system may be expanded to include analysis circuitry capable of processing the aligned ECG signals to determine the presence and magnitude of variations between the alternating signals such as T-wave alternans.

These and other features and advantages of the invention are described in detail below with reference to the figures in which like numbers indicate like elements.

BRIEF DESCRIPTION OF DRAWINGS

The foregoing and other advantages of the invention will become apparent upon reading the following detailed description and upon reference to the drawings in which:

FIG. 1 illustrates a typical application of a patient undergoing an electrocardiogram procedure and the components of an idealized electrocardiogram system in relation thereto;

FIG. 2 is a functional block diagram of a system representing a preferred embodiment of the present invention;

FIG. 6 is an ECG plot superimposing an odd and even heartbeat which has undergone alignment the preferred embodiment of the present invention.

DETAILED DESCRIPTION

Figure 3:
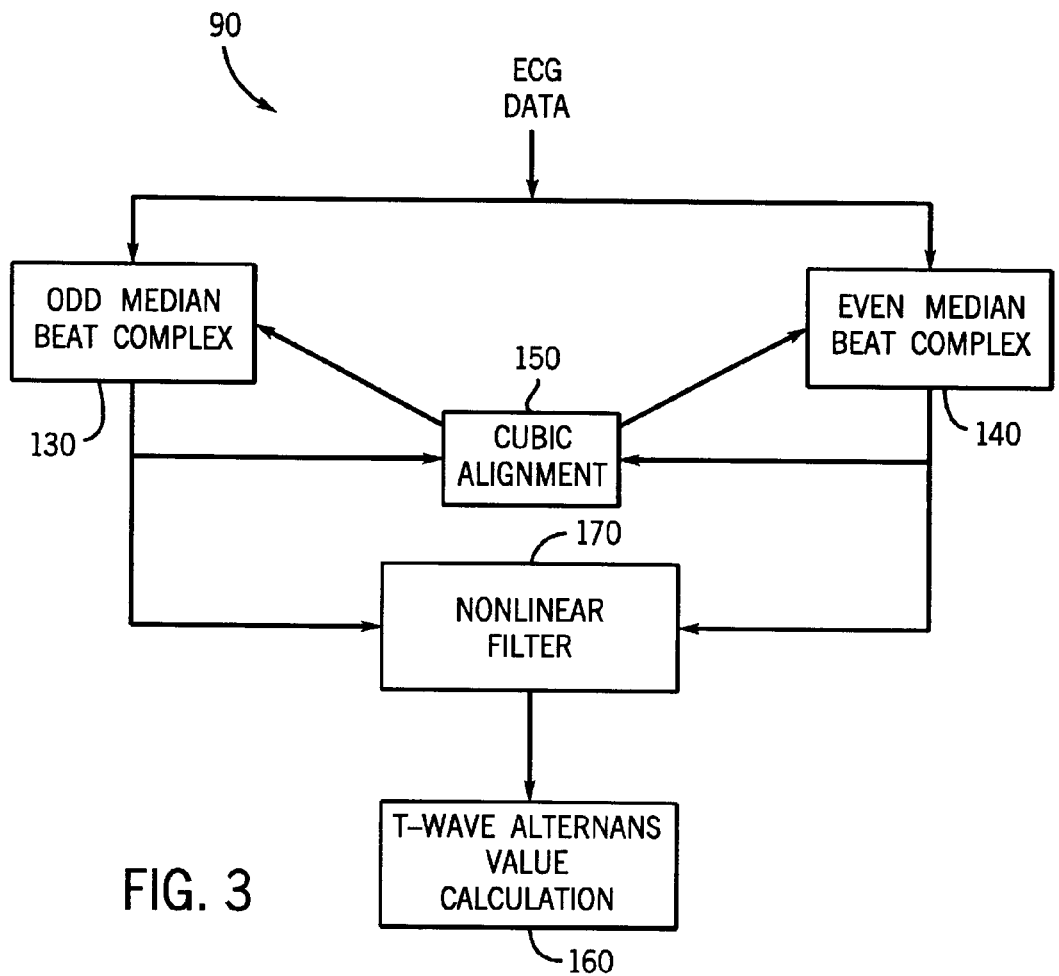
FIG. 3 is a block diagram of a method of collecting and analyzing alternating ECG signals representing a preferred embodiment of the present invention.

In the invention, a reference function is calculated and then applied to alternating heartbeat data to bring the odd and even heartbeats into alignment. The aligned heartbeats are then susceptible to comparative analysis to detect and quantify differences between the alternating heartbeats. In a preferred embodiment, the target cubic spline, the odd median cubic spline, and the even median cubic spline are calculated in the same manner, each of them comprising a pair of cubic splines which are determined as follows and where the following letter representations are used: T represents a reference time; t represents a variable time; y represents an amplitude in an ECG cycle, measured at some time, t; s(t) is the amplitude in a spline segment at time t calculated with a spline function.

An ECG cycle consists of samples. In a cycle, y is the amplitude of an ECG sample at point of time t. Similarly, $y_1$ is the amplitude of an ECG cycle when $t=T_1$.

Initially, three reference points are determined, $(T_1, y_1)$, $(T_2, y_2)$, $(T_3, y_3)$ such that $T_1<T_2<T_3$. Point $(T_1, y_1)$ is the point before the P-wave at time $T_1$. Point $(T_2, y_2)$ is the point before the QRS-complex at time $T_2$. Point $(T_3, y_3)$ is the point after the T-wave at time $T_3$. These three points are used to calculate two splines spanning the two regions defined by $T_1$, $T_2$, and $T_3$. Spline $s_1(t)$ is between $t=T_1$ and $t=T_2$. Spline $s_2(t)$ is between $t=T_2$ and $T_3$.

The following equations demonstrate the calculation of the two splines:

$$s_1(t)=a_1t^3+b_1t^2+c_1t+d_1 \quad (1)$$

$$s_2(t)=a_2t^3+b_2t^2+c_2t+d_2. \quad (2)$$

The coefficients a1, a2, b1, b2, c1, c2, d1 and d2 are calculated using the following derivatives of the two spline equations:

$$s_1'(t)=3a_1t^2 2b_1t+c_1 \Rightarrow s_1'(0)=c_1 \quad (3)$$

$$s_1''(t)=6a_1t+2b_1 \Rightarrow s_1''(0)=2b_1 \quad (4)$$

$$s_1'''(t)=6a_1 \Rightarrow s_1'''(0)=6a_1 \quad (5)$$

$$s_2'(t)=3a_2t^2+2b_2t+c_2 \Rightarrow s'(0)=c_2 \quad (6)$$

$$s_2''(t)=6a_2t+2b_2 \Rightarrow s_2''(0)=2b_2 \quad (7)$$

$$s_2'''(t)=6a_2 \Rightarrow s_2'''(0)=6a_2. \quad (8)$$

In order to create a smooth transition between the two splines the following conditions are stipulated:

$$s_1(T_2)=s_2(T_2) \quad (9)$$

$$s_1'(T_2)=s_2'(T_2), \text{ and} \quad (10)$$

$$s_1''(T_2)=s_2''(T_2). \quad (11)$$

In order to simplify this transition, $(T_2, y_2)$ is set to $(0,0)$ and:

$$s_1(0)=s_2(0)=0 \quad (12)$$

$$s_1'(0)=s_2'(0) \quad (13)$$

$$s_1''(0)=s_2''(0) \quad (14)$$

The first spline starts with:

$$s_1''(T_1)=0. \quad (15)$$

The second spline ends with:

$$s_2''(T_3)=0. \quad (16)$$

With conditions (12) through (16) in place, the coefficients $a_1$, $a_2$, $b_1$, $b_2$, $c_1$, $c_2$, $d_1$, and $d_2$ are calculated and substituted into equations (1) and (2). The $s_1(t)$ values are then calculated with the t values between $T_1$ and $T_2$ and the $s_2(t)$ values are then calculated with the t values between $T_2$ and $T_3$.

In a typical embodiment, the above mentioned equations would be implemented and solved by one or more processing circuits either dedicated to those functions or programmable via machine readable code, such as software, to perform those functions as part of a programmable ECG system.

Figure 4:
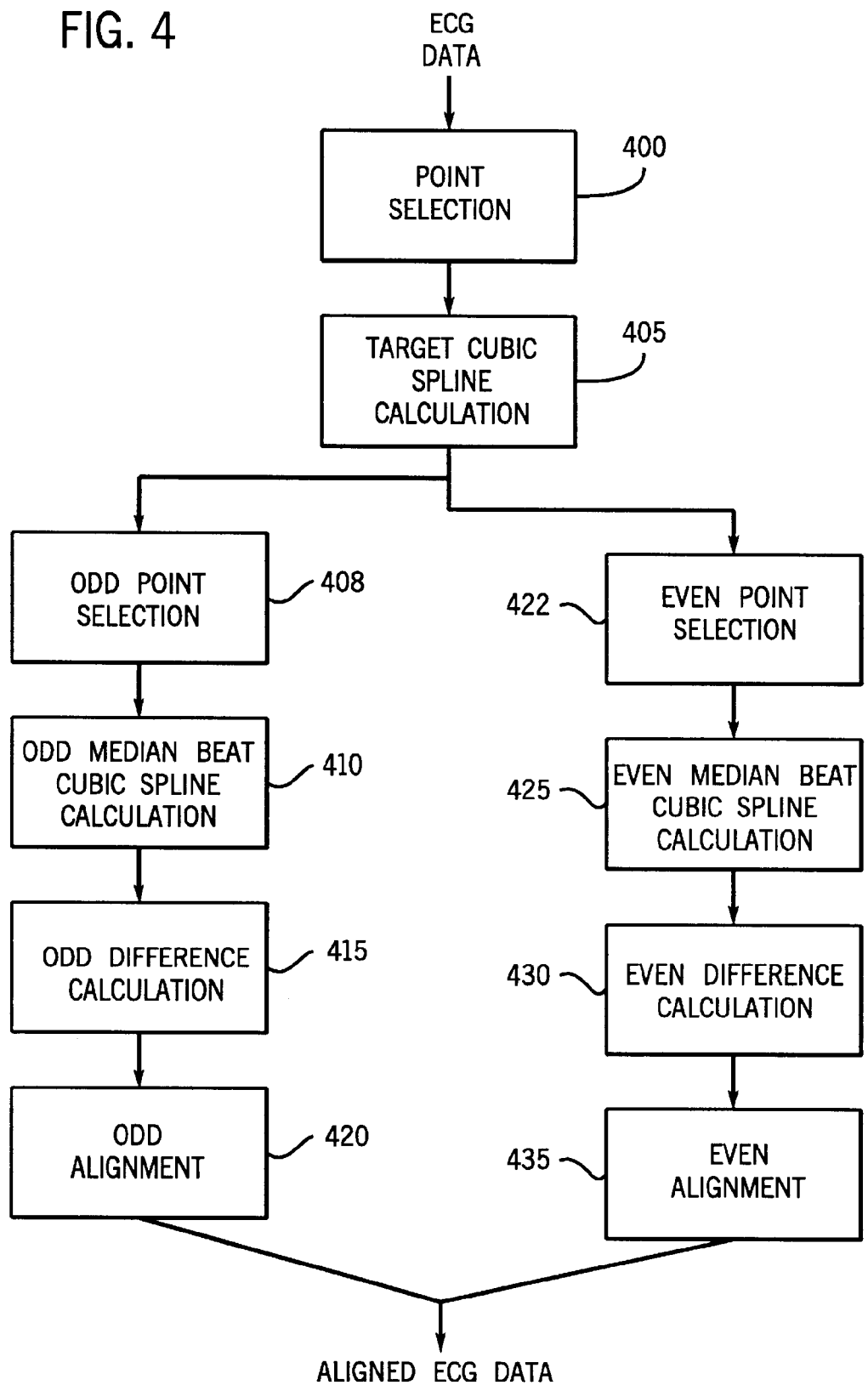
FIG. 4 is a flowchart illustrating the steps taken in collecting, analyzing and aligning alternating ECG data signals by the preferred embodiment of the present invention.
Figure 5:
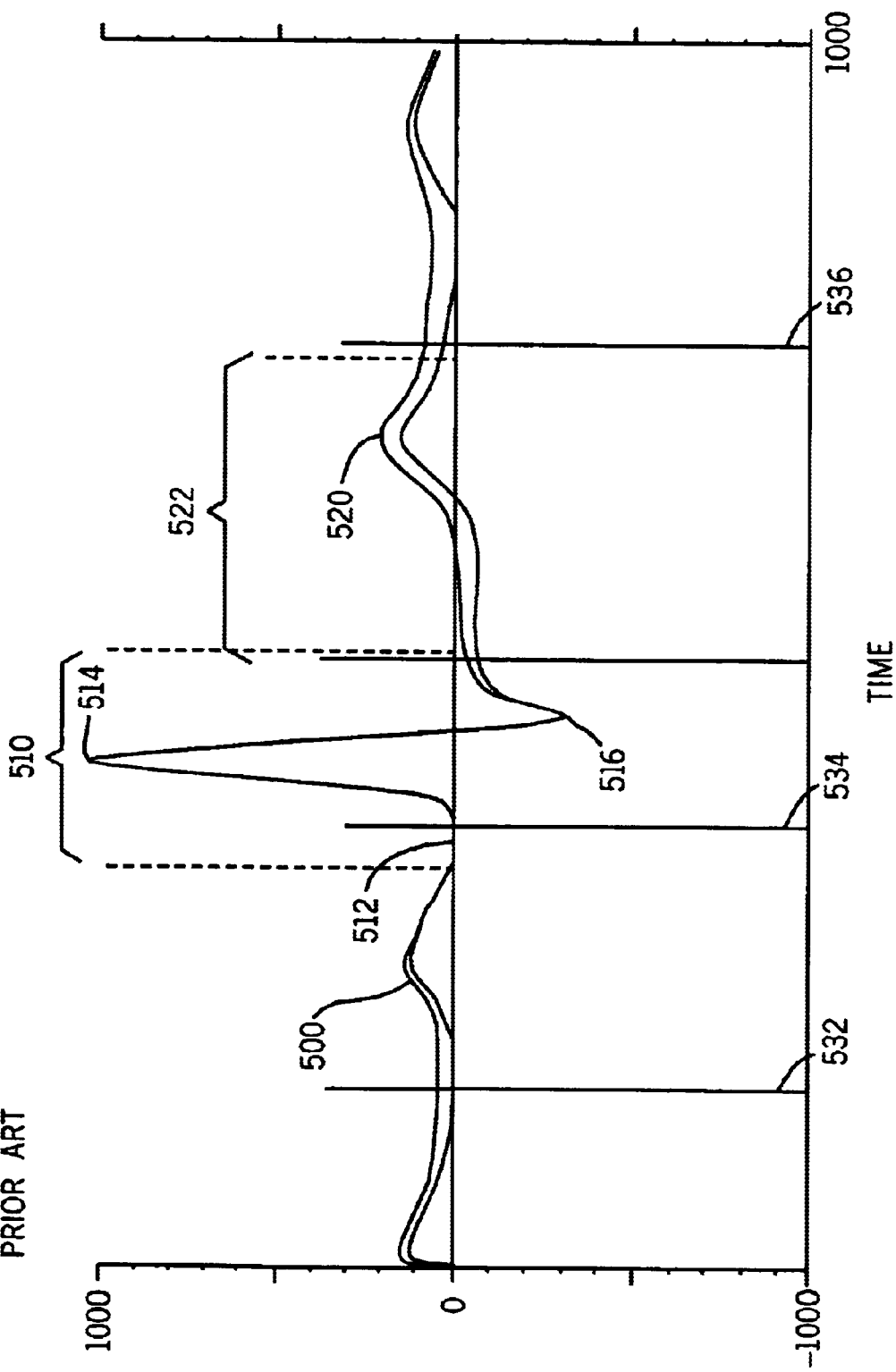
FIG. 5 is an ECG plot superimposing an odd and even heartbeat which has undergone baseline removal wander filtering by the prior art method.

Reference will first be made to FIG. 5 to allow the introduction of ECG related terminology. In FIG. 5, an odd and an even heartbeat are shown superimposed on an ECG plot. FIG. 5 depicts superimposed odd and even heartbeats after undergoing alignment by the prior art method. A P-wave deflection 500 is depicted which is due to the depolarization of the atria. A QRS-complex 510 is depicted which is due to the depolarization of the ventricles and which is composed of an isoelectric line 512, a R-wave deflection 514, and an S-wave deflection 516. A T-wave deflection 520 is also depicted and is due to the repolarization of the ventricles. An ST-segment 522 is defined by the region between the end of S-wave 516 and the beginning of T-wave 520. Because the present technique is concerned with alternans in ST-segment 522 as well as in T-wave 520, the term "T-wave alternans" in this disclosure includes both T-wave 520 and ST-segment 522. Also depicted in FIG. 5 are three reference times, $T_1$ (532), $T_2$ (534), and $T_3$ (536), which are discussed above in relation to the algorithm equations and which are also discussed in FIG. 4 in relation to the cubic alignment step of the present technique.

Referring now to a typical embodiment, as illustrated in FIG. 1, an ECG data series is collected from a patient 10 over a period of time. The ECG data series is collected in a manner common in the art and familiar to one skilled in the art. In particular, an ECG system 20 is connected by leads 22 and contact pads 21 to patient 10. Patient 10 may be monitored in either Holter, resting ECG, electrophysical test or exercise test systems or in other types of systems known in the art. ECG system 20 is comprised of a signal receiver 24 connected to leads 22, processing circuitry 26 performing the TWA calculation and alignment functions later described, display circuitry 28 transmitting signals to an output device such as a printer 32 or display unit 34 through an output interface 30, and memory circuitry 36 which can be accessed by signal receiver 24, processing circuitry 26, or display circuitry 28. The circuitry comprising ECG system 20 may be implemented in one or more computer systems or other processing systems and may be implemented using hardware, software, or a combination thereof. The circuitry comprising ECG system 20 is ideally interconnected along a communication infrastructure 38. In a preferred embodiment, the present technique is implemented via a program comprising configuration code for ECG system 20 and written in a machine readable code which can be accessed by the system off of a machine readable medium, such as a magnetic or optical disk, or over a configurable network connection. Additionally, components of the program or ECG data series may be accessed from a second machine readable medium if desired.

FIG. 2 depicts a functional block diagram of the components of a preferred embodiment of ECG system 20 and their interrelationships. An operator 50 interacts with the ECG system 20 by means of a user interface module 55. User interface module 55 is connected to monitoring module 60 which is comprised of signal receiver 24 and leads 22. Monitoring module 60 and user interface module 55 are in turn connected to processing module 65 which is comprised of at least processing circuitry 26. Processing module 65 and user interface module 55 are in turn connected to output module 70 which is comprised of at least display circuitry 28 and further possibly comprising an output interface 30 to a device such as a printer 32 or display unit 34.

The ECG system is further comprised of a memory module 75 comprising at least memory circuitry 36. Memory module 75 may include such components as standard RAM memory, magnetic storage media such as a hard disk drive, or optical storage media such as optical disks. Monitoring module 60 may be connected to memory module 75 such that signal data is passed from monitoring module 60 to memory module 75 for temporary or long term storage. Processing module 65 may also be connected to memory module 75 such that ECG signal data may be passed to or from processing module 65 to memory module 75. Finally, output module 70 may be connected to memory module 75 such that data may be passed from memory module 75 to output module 70. User interface module 55 may also be connected to memory module 75 but, in a preferred embodiment, instead interacts with memory module 75 via the other modules such as processing module 65 or monitoring module 60.

Referring now to FIG. 3, the functions generally performed by processing circuitry 26 are displayed as a block diagram and are designated generally by reference numeral 90. ECG data is received into the processing circuitry from either signal receiver 24, from an external data source (e.g. internet) or from memory circuitry 36. In turn, the processed output, either a TWA value, an aligned ECG signal or both are sent to display circuitry 28 or to memory circuitry 36.

The preferred embodiment encompasses a first and a second median beat complex. Ideally these two median beat representations separately, and exclusively, comprise the odd and the even beat data. As used herein, the term "median complex" refers to a median representation of one or more beats of the ECG data. While the median complex can represent only a single beat, it is preferred that a larger number of beats contribute to the median values of the complex. The resultant median complex represents an average of the samples of the beats (odd or even) which contribute to it. However in a preferred embodiment, the median complex is not a true average because the averaging is done so that the effect that any one beat can have on the median complex is limited. Instead a weighted function or average is used to determine the median complex. This weighted function increments the median complex by a fixed increment or $\frac{1}{32}$th the difference between the amplitude of the sample beat and the median complex, depending on the difference between the contributing beat and the median complex.

The ECG data is used to calculate the odd median complex and the even median complex in steps 130 and 140. In step 130, a first array is initialized with the median of a plurality of odd complex values. For example, the samples of the first beat of the ECG data may be used as the initial values of the odd median complex. Alternatively, if a previous ECG segment has been processed, the odd median values resulting from the calculation may be used as the initial odd median values. The odd beats of the ECG data are compared sample by sample with the odd median complex. Each odd beat (i.e., beats 1, 3, 5, 7, 9 and so on) is identified based on the first slope of the QRS-complex. In a preferred embodiment, a beat is identified as the ECG data occurring between a point 450 msec before the first slope of the QRS-complex to a point 550 msec after the slope of the QRS-complex for a total of 1.0 seconds of ECG data. At a sampling rate of 500 Hz, this provides 500 samples per beat. Thus, if the first beat is used to initialize the odd median complex, then 500 samples representing the third beat (i.e., the next odd beat) will be compared to the corresponding 500 samples in the odd median complex.

For each sample of an odd beat that is compared to a corresponding sample in the odd median complex, the result of the comparison is tested. If the sample of the current beat exceeds the corresponding value of the median complex by a predetermined amount then the corresponding value of the median complex is incremented by the predetermined amount. If the sample of the current odd beat does not exceed the corresponding value of the odd median complex by the predetermined amount then the corresponding value in the odd median complex is incremented by $\frac{1}{32}$th of the difference between the sample of the current odd beat and the corresponding value of the odd median complex.

These steps are repeated for each sample of each odd beat until the desired number of odd beats (i.e., at least one) are processed. The resultant odd median complex represents an average of the samples of the odd beats. The same process is than followed for the second array using the even beats.

Once the odd and even median complexes are computed they are aligned by cubic alignment step 150. Cubic alignment step 150 is depicted in greater detail in FIG. 4.

Referring now to FIG. 4, a flowchart of the implementation of cubic alignment step 150 is depicted. Cubic alignment step 150 is accomplished by a reference function which aligns both the even and odd median beat complexes. In a preferred embodiment, the reference function is a target cubic spline. This target cubic spline is calculated on the basis of three reference points located exactly between the odd and even median beats before P-wave 500 at $T_1$ (532), with $y_1=(y_{1(odd)}+y_{1(even)})/2$, before the QRS-complex 510 at $T_2$ (534), with $y_2=(y_{2(odd)}+y_{2(even)})/2$, and after T-wave 520 at $T_3$ (536), with $y_3=(y_{3(odd)}+y_{3(even)})/2$. These three reference times define two separate spans or regions for each beat processed, and define a common interval along the median complexes which can be aligned and compared. Selection of these three points is represented diagrammatically as point selection step 400.

After point selection step 400, target cubic spline (TCS) calculation step 405 is performed. The TCS calculation is comprised of equations (1) and (2) and solved using equations (3) through (16) on the basis of the points $(T_1, y_1)$, $(T_2, y_2)$, and $(T_3, y_3)$.

After the calculation of the TCS, an odd point selection step 408 and an odd median beat cubic spline calculation step 41 0 are performed. Odd point selection step 408 corresponds to point selection step 400. Three points on the odd median beat complex are selected which are located before P-wave 500 at $T_1$ (532), before the QRS-complex 510 at $T_2$ (534), and after T-wave 520 at $T_3$ (536). Calculation of an odd median beat cubic spline is then done similarly to the calculation of the TCS except the amplitude $y_1$ corresponding to $T_1$ of the odd median beat data is utilized so that $y_1$ equals $y_{1(odd)}$ at time $T_1$ (532). The points $y_2$ and $y_3$ are similarly derived.

The algorithm next calculates the difference between the odd median beat cubic spline and target cubic spline in odd difference calculation step 415. This difference is then subtracted from the odd median beat in odd alignment step 420. This subtraction (alignment) is done with every sample of the odd median beat so that every odd sample is corrected. The result is an odd median beat complex.

Similarly, an even point selection step 422 and an even median beat cubic spline calculation step 425 is performed such that $y_1$ equals $y_{1(even)}$ at time $T_1$ (532) of the even median beat complex. After calculation of the even median beat cubic spline, even difference calculation step 430 and even alignment step 435 are performed and correspond to their odd beat counterpart steps 415 and 420 respectively.

The cubic alignment is very tolerant to the location of the points. It yields very good results even when atrial repolarization or a short PR interval hides the isoelectric line before QRS-complex 510 or a merging T-wave 520 and P-wave 500 in the other two points hide the isoelectric T-P-interval.

By way of comparison, unaligned median beat complexes as processed by the prior art method are plotted in FIG. 5 while the same median beat complexes are plotted in FIG. 6 after alignment by the present invention. FIG. 6 also depicts the presence of a T-wave alternans 530 seen as the maximum difference between the superimposed portions of the T-waves of the successive beats. A comparison of FIGS. 5 and 6 demonstrates the elimination of false positive T-wave alternans by alignment of the odd and even median complexes achieved by the present technique. This alignment of the odd and even median beat complexes as taught by the present technique is significant to both the determination of and the quantification of T-wave alternans 530 events. While there is no current agreement upon a T-wave alterans threshold to determine the presence of a T-wave alternans event, one skilled in the art may decide upon an appropriate diagnostic reference value to apply in conjunction with the present invention as an appropriate T-wave alternans threshold value.

Returning now to FIG. 3, after cubic alignment step 150, a nonlinear filter step 170 and a TWA calculation step 160 are performed. In TWA calculation step 160 the aligned odd and even median beat complexes are compared to obtain an estimate of the amplitude of the beat-to-beat alternation in the ECG data. This estimate is the TWA value which is compared to some diagnostic reference value to determine if TWA is present. In a preferred embodiment of the invention, the comparison involves determining the maximum difference amount in amplitude ($|y_{(odd)}-y_{(even)}|$) between the corresponding values of the aligned odd and even median complexes in the region encompassing ST-segment 522 and T-wave 520.

When calculating the TWA value, high frequency noise can falsify the TWA value substantially. Therefore, a nonlinear filter step 170 is performed. The nonlinear filter has two 20 ms windows, one in the odd the other in the even median beat, and both starting at the end of QRS-complex 510. The minimal difference amount between all amplitudes of the windows is selected and stored, and then the windows are moved one step towards the end of T-wave 520. The minimal difference amount is selected again and stored, and the windows are moved once more. The procedure is repeated until the windows reach the end of T-wave 520. In the stored values the high frequency noise is filtered out. The TWA value is then calculated by searching for the maximal difference in the stored values.

It should be noted that, for the first measurement interval, the odd beats are beats 1, 3, 5, 7 and so forth to the end of the measurement interval. Similarly, the even beats for the first measurement interval are 2, 4, 6, 8 and so forth to the end of the measurement interval. For all subsequent measurement intervals, if the last beat of the immediately preceding measurement interval was even, the odd beats will be beats 1, 3, 5, 7, etc. and the even beats will be beats 2, 4, 6, 8, etc. However if the last beat of the immediately preceding measurement interval was odd, then the odd beats will be beats 2, 4, 6, 8, etc. and the even beats will be beats 1, 3, 5, 7, etc. This latter rule preserves the relative groupings of odd and even beats throughout an ECG data sample if multiple measurement intervals are involved in data collection.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of measuring T-Wave alternans by aligning alternating heartbeats from a series of electrocardiogram signals comprising:

determining a first ECG data series comprising one or more beats;

determining a second ECG data series comprising one or more beats such that the beats of the second ECG data series alternate with the one or more beats of the first ECG data series;

deriving a reference function from a third ECG data series such that the third ECG data series comprises at least a portion of the first ECG data series and at least a portion of the second ECG data series;

deriving a first ECG data series reference function from the first ECG data series;

deriving a second ECG data series reference function from the second ECG series;

calculating a first difference between the reference function and the first ECG data series reference function;

calculating a second difference between the reference function and the second ECG data series reference function;

determining an aligned first ECG data series by adjusting the first ECG data series by the first difference;

determining an aligned second ECG data series by adjusting the second ECG data series by the second difference;

determining a first median beat representation from the aligned first ECG data series and a second median beat representation from the aligned second ECG data series; and determining a maximum amplitude difference between the first median beat representation and the second median beat representation within a common interval.

2. The method as recited in claim 1, further comprising determining the first median beat representation as a weighted function of the aligned first ECG data series and determining the second median beat representation as the weighted function of the aligned second ECG data series.

3. The method recited in claim 1, further comprising deriving the reference function as a target cubic spline.

4. The method as recited in claim 3, further comprising calculating the target cubic spline using one or more averages of one or more pairs of successive heartbeats.

5. The method as recited in claim 1, further comprising calculating the first ECG data series reference function as a first cubic spline and the second ECG data series reference function as a second cubic spline.

6. The method as recited in claim 1, further comprising comparing the maximum amplitude difference to a diagnostic reference value.

7. The method as recited in claim 6, wherein the common interval comprises a ST-segment and a T-wave of the first median beat representation and of the second median beat representation and wherein the diagnostic reference value is a T-wave alternans threshold.

8. The method as recited in claim 7, further comprising the step of applying a nonlinear filter to the first median beat representation and to the second median beat representation.

9. A method of determining a reference function from a series of electrocardiogram signals comprising:

determining a first ECG data series comprising one or more beats;

determining a second ECG data series comprising one or more beats such that the second ECG data series comprises those one or more beats not comprising the first ECG data series; and determining a reference function derived from a third ECG data series such that the third ECG data series comprises at least a portion of the first ECG data series and at least a portion of the second ECG data series.

10. The method recited in claim 9, further comprising constituting the first ECG data series with beats alternating with the beats of the second ECG data series such that successive beats are excluded from the first ECG data series.

11. The method recited in claim 10, further comprising deriving a first median beat representation of the one or more beats of the first ECG data series and deriving a second median beat representation of the one or more beats of the second ECG data series.

12. The method as recited in claim 11, further comprising determining the first median beat representation as a weighted function of the one or more beats of the first ECG data series and determining the second median beat representation as the weighted function of the one or more beats of the second ECG data series.

13. The method recited in claim 12, further comprising adjusting the weighted function by an amount determined by the difference between the median beat sample and the according sample of the current beat.

14. The method recited in claim 11, further comprising determining the reference function as a target cubic spline.

15. The method as recited in claim 14, further comprising calculating the target cubic spline using one or more averages of one or more pairs of successive heartbeats.

16. The method as recited in claim 14, further comprising determining a first median beat representation function and a second median beat representation function.

17. The method as recited in claim 16, further comprising calculating the first median representation function as a first median beat cubic spline and the second median representation function as a second median beat cubic spline.

18. The method as recited in claim 17, further comprising subtracting the target cubic spline from the first median beat cubic spline to derive a first difference and subtracting the target cubic spline from the second median beat cubic spline to derive a second difference.

19. The method as recited in claim 18, further comprising correcting the one or more beats comprising the first ECG data series by the first difference and correcting the one or more beats comprising the second ECG data series by the second difference such that the first median beat representation is derived from the corrected one or more beats of the first ECG data series and the second median beat representation is derived from the corrected one or more beats of the second ECG data series.

20. The method as recited in claim 19, further comprising finding a maximum difference amount between the first median beat representation and the second median beat representation within a common interval.

21. The method as recited in claim 20, further comprising comparing the maximum difference amount to a diagnostic reference value.

22. The method as recited in claim 21, wherein the common interval comprises a ST-segment and a T-wave of the first median beat representation and of the second median beat representation and wherein the diagnostic reference value is a T-wave alternans threshold.

23. The method recited in claim 9, further comprising determining the reference function as a target cubic spline.

24. The method as recited in claim 23, further comprising calculating the target cubic spline using one or more averages of one or more pairs of successive heartbeats.

25. A computer program for determining an electrocardiogram reference function, the computer program comprising:

a machine readable medium for supporting machine readable code; and configuration code stored on the machine readable medium for determining a reference function derived from an ECG data series comprising at least a portion of a first ECG data series and at least a portion of a second ECG data series such that the first and second ECG data series are mutually exclusive of one another.

26. The computer program of claim 25, wherein the configuration code refers to additional configuration code stored on a second machine readable medium, additional configuration code comprising the ECG data series.

27. The computer program of claim 25, wherein the configuration code is installed on the machine readable medium over a configurable network connection.

28. The computer program of claim 25, wherein the ECG data series comprises two or more successive heartbeats, and wherein the configuration code comprises code for determining a reference function calculated as a target cubic spline after at least partial processing of the ECG data series.

29. A system for measuring T-Wave alternans by aligning alternating heartbeats from a series of electrocardiogram signals, comprising:
 a monitoring module;
 a memory module;
 an output module; and
 a processing module comprising one or more processing circuits configured to
  determine a first ECG data series comprising one or more beats;
  determine a second ECG data series comprising one or more beats such
 that the beats of the second ECG data series alternate with the one or more beats of the first ECG data series;
  derive a reference function from a third ECG data series such that the third ECG data series comprises at least a portion of the first ECG data series and at least a portion of the second ECG data series;
  derive a first ECG data series reference function from the first ECG data series;
  derive a second ECG data series reference function from the second ECG series;
  calculate a first difference between the reference function and the first ECG data series reference function;
  calculate a second difference between the reference function and the second ECG data series reference function;
  determine an aligned first ECG data series by adjusting the first ECG data series by the first difference;
  determine an aligned second ECG data series by adjusting the second ECG data series by the second difference;
  determine a first median beat representation from the aligned first ECG data series and a second median beat representation from the aligned second ECG data series; and
  determine a maximum amplitude difference between the first median beat representation and the second median beat representation within a common interval.

30. The system as recited in claim 29, wherein the processing module is further configured to determine the first median beat representation as a weighted function of the aligned first ECG data series and to determine the second median beat representation as the weighted function of the aligned second ECG data series.

31. The system as recited in claim 29, wherein the processing module is further configured to derive the reference function as a target cubic spline.

32. The system as recited in claim 31, wherein the processing module is further configured to calculate the target cubic spline using one or more averages of one or more pairs of successive heartbeats.

33. The system as recited in claim 29, wherein the processing module is further configured to calculate the first ECG data series reference function as a first cubic spline and the second ECG data series reference function as a second cubic spline.

34. The system as recited in claim 29, wherein the processing module is further configured to compare the maximum amplitude difference to a diagnostic reference value.

35. The system as recited in claim 34, wherein the common interval comprises a ST-segment and a T-wave of the first median beat representation and of the second median beat representation and wherein the diagnostic reference value is a T-wave alternans threshold.

36. The system as recited in claim 35, wherein the processing module is further configured to apply a nonlinear filter to the first median beat representation and to the second median beat representation.

37. A system for measuring T-Wave alternans, comprising:
 a monitoring module;
 a memory module;
 an output module;
 a processing module;
 means for determining a first ECG data series comprising one or more beats;
 means for determining a second ECG data series comprising one or more beats such that the beats of the second ECG data series alternate with the one or more beats of the first ECG data series;
 means for deriving a reference function from a third ECG data series such that the third ECG data series comprises at least a portion of the first ECG data series and at least a portion of the second ECG data series;
 means for deriving a first ECG data series reference function from the first ECG data series;
 means for deriving a second ECG data series reference function from the second ECG series;
 means for calculating a first difference between the reference function and the first ECG data series reference function;
 means for calculating a second difference between the reference function and the second ECG data series reference function;
 means for determining an aligned first ECG data series by adjusting the first ECG data series by the first difference;
 means for determining an aligned second ECG data series by adjusting the second ECG data series by the second difference;
 means for determining a first median beat representation from the aligned first ECG data series and a second median beat representation from the aligned second ECG data series; and
 means for determining a maximum amplitude difference between the first median beat representation and the second median beat representation within a common interval.

38. The system as recited in claim 37, further comprising means for determine the first median beat representation as a weighted function of the aligned first ECG data series and to determine the second median beat representation as the weighted function of the aligned second ECG data series.

39. The system as recited in claim 37, further comprising means for deriving the reference function as a target cubic spline.

40. The system as recited in claim 39, further comprising means for calculating the target cubic spline using one or more averages of one or more pairs of successive heartbeats.

41. The system as recited in claim 37, further comprising means for calculating the first ECG data series reference function as a first cubic spline and the second ECG data series reference function as a second cubic spline.

42. The system as recited in claim 37, further comprising means for comparing the maximum amplitude difference to a diagnostic reference value.

43. A system for determining a reference function from a series of electrocardiogram signals, comprising:
   a monitoring module;
   a memory module;
   an output module; and
   a processing module comprising one or more processing circuits configured to:
      determine a first ECG data series comprising one or more beats;
      determine a second ECG data series comprising one or more beats such that the second ECG data series comprises those one or more beats not comprising the first ECG data series; and
      determine a reference function derived from a third ECG data series such that the third ECG data series comprises at least a portion of the first ECG data series and at least a portion of the second ECG data series.

44. The system as recited in claim 43, wherein the processing module is further configured to constitute the first ECG data series with beats alternating with the beats of the second ECG data series such that successive beats are excluded from the first ECG data series.

45. The system as recited in claim 44, wherein the processing module is further configured to derive a first median beat representation of the one or more beats of the first ECG data series and to derive a second median beat representation of the one or more beats of the second ECG data series.

46. The system as recited in claim 45, wherein the processing module is further configured to determine the first median beat representation as a weighted function of the one or more beats of the first ECG data series and to determine the second median beat representation as the weighted function of the one or more beats of the second ECG data series.

47. The system as recited in claim 46, wherein the processing module is further configured to adjust the weighted function by an amount determined by the difference between the median beat sample and the according sample of the current beat.

48. The system as recited in claim 45, wherein the processing module is further configured to determine the reference function as a target cubic spline.

49. The method as recited in claim 48, wherein the processing module is further configured to calculate the target cubic spline using one or more averages of one or more pairs of successive heartbeats.

50. The method as recited in claim 48, wherein the processing module is further configured to determine a first median beat representation function and a second median beat representation function.

51. The method as recited in claim 50, wherein the processing module is further configured to calculate the first median representation function as a first median beat cubic spline and the second median representation function as a second median beat cubic spline.

52. The method as recited in claim 51, wherein the processing module is further configured to subtract the target cubic spline from the first median beat cubic spline to derive a first difference and subtracting the target cubic spline from the second median beat cubic spline to derive a second difference.

53. The method as recited in claim 52, wherein the processing module is further configured to correct the one or more beats comprising the first ECG data series by the first difference and correcting the one or more beats comprising the second ECG data series by the second difference such that the first median beat representation is derived from the corrected one or more beats of the first ECG data series and the second median beat representation is derived from the corrected one or more beats of the second ECG data series.

54. The method as recited in claim 53, wherein the processing module is further configured to find a maximum difference amount between the first median beat representation and the second median beat representation within a common interval.

55. The method as recited in claim 54, wherein the processing module is further configured to compare the maximum difference amount to a diagnostic reference value.

56. The method as recited in claim 55, wherein the common interval comprises a ST-segment and a T-wave of the first median beat representation and of the second median beat representation and wherein the diagnostic reference value is a T-wave alternans threshold.

57. The system as recited in claim 43, wherein the processing module is further configured to determine the reference function as a target cubic spline.

58. The system as recited in claim 57, wherein the processing module is further configured to calculate the target cubic spline using one or more averages of one or more pairs of successive heartbeats.

59. A system for determining a reference function from a series of electrocardiogram signals, comprising:
   a monitoring module;
   a memory module;
   an output module;
   a processing module comprising one or more processing circuits;
   means for determining a first ECG data series comprising one or more beats;
   means for determining a second ECG data series comprising one or more beats such that the second ECG data series comprises those one or more beats not comprising the first ECG data series; and
   means for determining a reference function derived from a third ECG data series such that the third ECG data series comprises at least a portion of the first ECG data series and at least a portion of the second ECG data series.

60. The system as recited in claim 59, further comprising means for determining the reference function as a target cubic spline.

61. The system as recited in claim 60, further comprising means for calculating the target cubic spline using one or more averages of one or more pairs of successive heartbeats.

* * * * *